US00PP31397P2

(12) United States Plant Patent
Egger

(10) Patent No.: US PP31,397 P2
(45) Date of Patent: Jan. 21, 2020

(54) ***PHYGELIUS* PLANT NAMED 'TNPHYCDR'**

(50) Latin Name: ***Phygelius* x *rectus***
Varietal Denomination: TNPHYCDR

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,831

(22) Filed: Jan. 18, 2019

(51) Int. Cl.
*A01H 5/02* (2018.01)
*A01H 6/00* (2018.01)

(52) U.S. Cl.
USPC ..... Plt./468
CPC ..... *A01H 6/00* (2018.05)

(58) Field of Classification Search
USPC ..... Plt./468
CPC ..... A01H 5/02
See application file for complete search history.

(56) References Cited

PUBLICATIONS https://issuu.com/monrovia4/docs/monrovia_tool_ kit_aug_20_ final; Aug. 30, 2018; 4 pages.*

* cited by examiner

*Primary Examiner* — Kent L Bell
(74) *Attorney, Agent, or Firm* — Klarquist Sparkman, LLP

(57) ABSTRACT

A new and distinct cultivar of *Phygelius* plant characterized by medium size deep red flowers, a long bloom time, an upright, well branched habit, with multiple crowns from the base, clean-looking, deep green foliage, and excellent vigor.

1 Drawing Sheet

Botanical denomination: *Phygelius* x *rectus*.
Variety designation: 'TNPHYCDR'.
Trade Designation: COLORBURST™Deep Red.

BACKGROUND OF THE INVENTION

The present invention relates to a new and distinct cultivar of *Phygelius*, given the name, 'TNPHYCDR'. *Phygelius* is in the family Scrophulariaceae. *Phygelius* x *rectus* 'TNPHYCDR' is from a controlled cross using *Phygelius* '3-2', a proprietary, unnamed plant as the seed parent, and *Phygelius* '3-5', a proprietary, unnamed plant as the pollen parent. It was part of a controlled breeding program to produce upright, compact habits with high flower count. This cultivar was selected for the medium size flowers, intense deep red flower color, upright and well branched habit, multiple crowns from the base, extended bloom time, and and clean-looking deep green foliage.

Compared to the seed parent, *Phygelius* '3-2', the new cultivar has a deep red flower color rather than rose-red.

Compared to the seed parent, *Phygelius* '3-5', the new cultivar has a more upright habit. Compared to *Phygelius* x *rectus* TIE DYE® 'Radiant Red', an unpatented plant, the new cultivar has intense deep red rather than rosy red flowers.

Compared to *Phygelius* x *aequalis* CROFTWAY™ Red Emperor 'Croredemp' (EU PVR granted EU20334), the new cultivar has intense, deep red flowers rather than rose red flowers.

Compared to *Phygelius* x *rectus* 'Red Alert', an unpatented plant, the new cultivar has a higher flower count and deep red rather than scarlet red flowers.

*Phygelius* x *rectus* 'TNPHYCDR' is uniquely distinguished by its:

1. medium size, intense, deep red flowers,
2. high flower count and long bloom time,
3. upright, well branched habit, with multiple crown from the base,
4. clean-looking, deep green foliage, and,
5. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of a two-year-old *Phygelius* ('TNPHYCDR') in the summer in Canby, Oreg.

FIG. 2 shows a close up of a three-year-old *Phygelius* ('TNPHYCDR') in bloom growing in full sun in the garden in June in Canby, Oreg.

DETAILED PLANT DESCRIPTION

The following is a detailed description of the new *Phygelius* cultivar based on observations of a 3-year-old specimen grown outside in a trial garden in Canby, Oreg. in July.

The color descriptions are all based on The Royal Horticultural Society Colour Chart, 5th edition, 2007, except where general color terms of ordinary dictionary significance are used.

Plant:

*Type.*—Semi-evergreen subshrub.

*Form.*—Upright, branching.

*Cold hardiness.*—USDA Zone 7-10.

*Size.*—Grows to 94 cm tall and 95 cm wide.

*Vigor.*—Excellent.

*Stem number.*—16 main stems from the crown.

*Stem.*—Upright, grows to 73 cm long and 8 cm wide (at the base), glabrous, internodes grow to 8.5 cm long, Greyed Purple 187A blending to between Black 203A and Brown 200A near base.

*Rooting.*—Plants root easily from stem cuttings.

Leaf:

*Type.*—Simple.

*Arrangement.*—Opposite.

*Shape.*—Ovate to ovate lanceolate.

*Venation.*—Pinnate.

*Margins.*—Serrate.

*Apex.*—Acute.

*Base.*—Cuneate.

*Blade, size.*—Grows to 7 cm long and 4.6 cm wide.

*Petiole.*—Grows to 2.9 cm long and 0.4 cm wide, Greyed Purple 187A.

*Surface texture.*—Glabrous on both sides.

*Leaf color.*—Topside closest to Green N137A with main vein at base Green 137C, bottom side Green 138B.

Inflorescence:

*Type.*—One-sided, pyramidal panicle with pendulous flowers.

*Number of flowers per inflorescence.*—About 120.

*Size of inflorescence.*—Grows to 31 cm long and 12 cm wide.

*Peduncle.*—Grows to 2 cm long and 0.5 cm wide, glabrous, between Greyed Purple 187A.

*Pedicel.*—Grows to 1.1 cm long and 1 mm wide, glabrous, Greyed Purple 187A.

*Bloom period.*—Mid June to frost in Canby, Oreg.

Flower bud:

*Size.*—4.3 cm long and 0.8 cm wide at the widest area.

*Description.*—Tubular, pendulous.

*Color.*—Closest to Red 53B.

Flower:

*Type.*—Zygomorphic, perfect.

*Shape.*—Tubular.

*Size.*—Grows to 5.3 cm long and 2 cm wide.

*Corolla description.*—Grows to 4.9 cm long and 2 cm wide; both sides glabrous; tube 3.5 cm long, swollen to 5 cm wide on bottom side for 0.5 cm under the calyx then narrows to 0.4 cm wide and expanding to 1.1 cm wide below the lobes; 5 lobes, reflexed, oblong, tips obtuse, margins entire, lobes 0.5 cm long and 0.5 cm wide; outside Red 53B, inside Red 53B on lobes for 0.2 cm, Yellow 13C ring extending into tube.

*Calyx description.*—0.8 cm deep and 0.8 cm wide, 5 spreading, slightly reflexed lobes cut almost to the base, glabrous inside and out, each lobe lanceolate in shape, 0.7 cm long and to 0.2 cm wide, margins entire, tip acute, closest to Greyed Purple 187A.

*Pistil description.*—1, 5.2 cm long, ovary 0.5 cm long and 0.3 cm wide, Greyed Purple 187A; style 4.5 cm long and less than 1 mm wide, Red Purple 60A; stigma 1 mm Red Purple 59A.

*Stamen description.*—4, filaments: two short 1.5 cm long and two long 2 cm and 1 mm wide, Greyed Purple 187A, anthers 0.3 cm long and 0.2 cm wide, Brown N200A.

*Pollen.*—None seen.

*Fragrance.*—None.

*Lastingness.*—A flower lasts about a week on a plant.

Fruit:

*Type.*—Capsule, curved.

*Fertility.*—Poor.

*Size.*—1 cm deep and 5 mm wide, stigma 3.5 cm long.

*Color.*—Brown 200D.

Seed: None seen.

Pests and diseases: Plants of the new *Phygelius* have not been observed to be resistant to pathogens and pests common to *Phygelius*.

I claim:

1. A new and distinct cultivar of *Phygelius* plant substantially as shown and described.

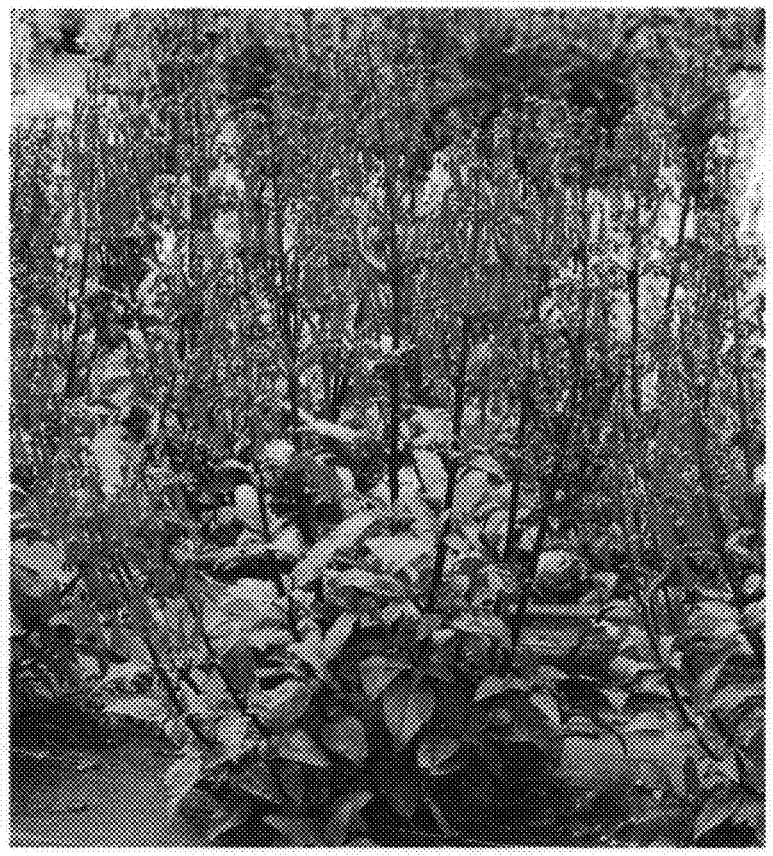
Fig. 1
Fig. 2
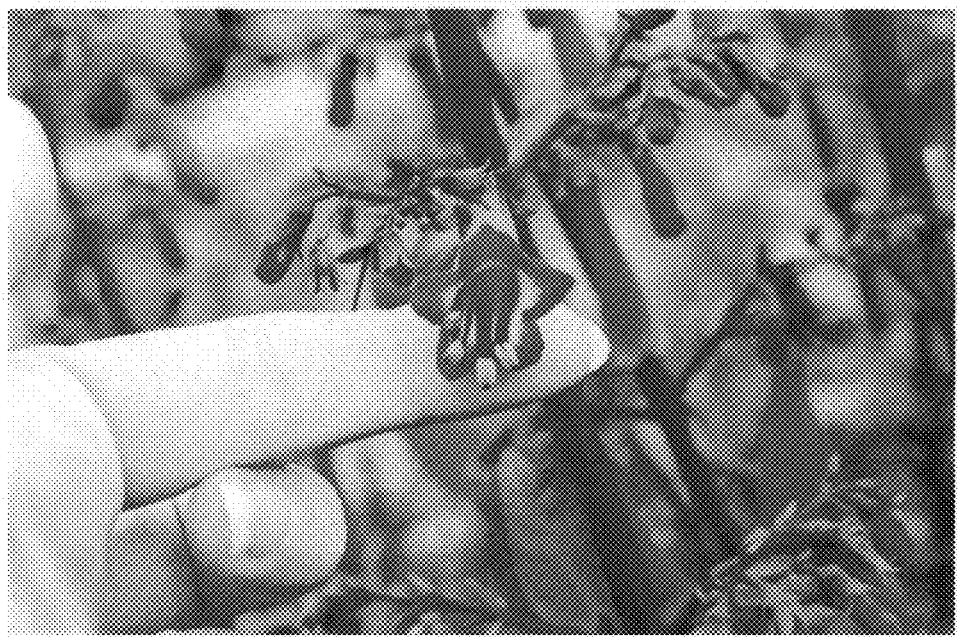

* * * * *